United States Patent
Labyed et al.

(10) Patent No.: US 10,159,466 B2
(45) Date of Patent: Dec. 25, 2018

(54) SPARSE TRACKING IN ACOUSTIC RADIATION FORCE IMPULSE IMAGING

(71) Applicant: Siemens Medical Solutions USA, Inc., Malvern, PA (US)

(72) Inventors: Yassin Labyed, Issaquah, WA (US); David P. Duncan, Renton, WA (US); Stephen J. Hsu, Issaquah, WA (US); Seungsoo Kim, Sammamish, WA (US); Liexiang Fan, Sammamish, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 15/873,633

(22) Filed: Jan. 17, 2018

(65) Prior Publication Data

US 2018/0153516 A1    Jun. 7, 2018

Related U.S. Application Data (62) Division of application No. 14/595,127, filed on Jan. 12, 2015, now Pat. No. 9,907,539.

(51) Int. Cl.
*A61B 8/08* (2006.01)
*G01S 15/89* (2006.01)
(Continued)

(52) U.S. Cl.
CPC .......... *A61B 8/485* (2013.01); *A61B 8/5207* (2013.01); *A61B 8/5215* (2013.01);
(Continued)

(58) Field of Classification Search
CPC ..... A61B 8/485; A61B 8/5215; A61B 8/5207; A61B 8/461; G01S 7/52042; G01S 7/52022; G01S 7/52071; G01S 15/8977
See application file for complete search history.

(56) References Cited

U.S. PATENT DOCUMENTS 8,197,408 B2   6/2012  Fan et al.
9,332,962 B2   5/2016  Kim et al.
(Continued)

FOREIGN PATENT DOCUMENTS

CN   103431874 A   12/2013
CN   104042247     9/2014
(Continued)

OTHER PUBLICATIONS

Dahl, et al, "A Parallel Tracking Method for Acoustic Radiation Force Impulse Imaging," IEEE Transaction on Ultrasonics, Ferroelectrics, and Frequency Control; vol. 54, No. 2; pp. 301-3012.
(Continued)

*Primary Examiner* — Bo J Peng (57) ABSTRACT

Sparse tracking is used in acoustic radiation force impulse imaging. The tracking is performed sparsely. The displacements are measured only one or a few times for each receive line. While this may result in insufficient information to determine the displacement phase shift and/or maximum displacement over time, the resulting displacement samples for different receive lines as a function of time may be used together to estimate the velocity, such as with a Radon transform. The estimation may be less susceptible to noise from the scarcity of displacement samples by using compressive sensing.

9 Claims, 7 Drawing Sheets

(51) Int. Cl.
  *G01S 7/52*  (2006.01)
  *A61B 8/00*  (2006.01)
(52) U.S. Cl.
  CPC ...... *G01S 7/52022* (2013.01); *G01S 7/52071* (2013.01); *G01S 15/8977* (2013.01); *A61B 8/461* (2013.01); *G01S 7/52042* (2013.01)

(56) References Cited

U.S. PATENT DOCUMENTS

| | | | |
|---|---|---|---|
| 2005/0215899 A1* | 9/2005 | Trahey | A61B 5/0048 600/439 |
| 2006/0029279 A1 | 2/2006 | Donoho | |
| 2009/0216119 A1 | 8/2009 | Fan et al. | |
| 2010/0016718 A1 | 1/2010 | Cezeaux et al. | |
| 2010/0138163 A1* | 6/2010 | Gallippi | A61B 8/485 702/19 |
| 2013/0218011 A1 | 8/2013 | Benson et al. | |
| 2014/0088421 A1 | 3/2014 | Guzina et al. | |
| 2015/0010222 A1 | 1/2015 | Provost et al. | |

FOREIGN PATENT DOCUMENTS

| | | |
|---|---|---|
| KR | 20140112453 A | 9/2014 |
| WO | WO2008141220 | 11/2008 |

OTHER PUBLICATIONS

Haltmeier, et al., "Compressed Sensing and Sparsity in Photoacoustic Tomography," Journal of Optics, vol. 18, No. 11, Published Oct. 20, 2016.

Search Report issued by Institut National De La Propriete Industrielle in corresponding application FR1600058, dated Mar. 20, 2018.

* cited by examiner

Full sampling spectrum

FIG. 9

Sparse sampling spectrum

FIG. 10

Reconstructed Sparse sampling spectrum

FIG. 11 inverse reconstructed data

FIG. 12

Radon Transform Reconstructed CS Data

SPARSE TRACKING IN ACOUSTIC RADIATION FORCE IMPULSE IMAGING

CROSS-REFERENCE TO RELATED APPLICATION

This application is a divisional and claims benefit of priority under 35 USC § 120 to pending U.S. patent application Ser. No. 14/595,127, filed Jan. 12, 2015.

BACKGROUND

The present embodiments relate to acoustic radiation force impulse (ARFI) imaging. For example, by transmitting an ARFI excitation pulse, ultrasound may be used to displace tissue directly or through generation of a shear or longitudinal wave. The displacement resulting from the wave generated by the excitation pulse may be measured using further ultrasound scanning or tracking.

To determine the velocity of the generated shear wave in tissue, displacements are estimated over time for each location. The maximum displacement over time and/or the relative phase shift in displacement temporal profiles between locations is found. The number of locations that can be tracked simultaneously depends on the maximum number of simultaneous receive beams provided by the system beamformer. To increase the size of the tracking area, more simultaneous receive beams are required (e.g., a costly, newer system is used) or repeated ARFI pushes are used to sample other tracking locations.

Excitation pulses are repeated to measure displacement at different laterally spaced locations. Depending on the size of the tracking area and the number of simultaneous receive beams used in tracking, many ARFI push transmissions may be required. However, the repetition of ARFI pulses may cause undesired transducer heating and introduce delays in scanning.

BRIEF SUMMARY

By way of introduction, the preferred embodiments described below include methods, instructions, and systems for sparse tracking in acoustic radiation force impulse imaging. The tracking is performed sparsely. The displacements are measured only one or a few times for each receive line. While this may result in insufficient information to determine the displacement phase shift and/or maximum displacement over time, the resulting displacement samples for different receive lines as a function of time may be used together to estimate the velocity, such as with a Radon transform. The estimation may be less susceptible to noise from the scarcity of displacement samples by using compressive sensing.

In a first aspect, a method is provided for sparse tracking in acoustic radiation force impulse imaging. An ultrasound scanner transmits an acoustic radiation force impulse into tissue of a patient along a first line. The ultrasound scanner tracks a wave generated in response to the transmitting with four or fewer receive beams along each of a plurality of tracking lines spaced from the first line. The displacement for each of the tracking lines is determined. The displacements are a sparse displacement sampling of the tracking lines. The sparse displacement samples are processed using a compressive sensing reconstruction algorithm to generate the significant Fourier coefficients of the 2D Fourier Transform of the displacement map (lateral position vs slow time). The Inverse Fourier Transform is applied to the Fourier coefficients to reconstruct the fully-sampled displacement map. The results of inverse Fourier transformation are Radon transformed. A velocity of the wave is calculated from results of the Radon transforming. An image of the velocity is generated.

In a second aspect, a non-transitory computer readable storage medium has stored therein data representing instructions executable by a programmed processor for sparse tracking in acoustic radiation force impulse imaging. The storage medium includes instructions for: measuring, using an ultrasound scanner, displacements in response to a single excitation pulse, the displacements measured at random locations over time; determining a velocity of a wave generated by the single excitation pulse from the displacements; and outputting the velocity.

In a third aspect, a system is provided for sparse tracking in acoustic radiation force impulse imaging. A transmit beamformer is configured to generate an excitation pulse, and a receive beamformer is configured to sparsely track displacements responsive to the excitation pulse. The sparsely tracked displacements are distributed by receive line over sample time such that no displacements are provided for more than half or more than ¼ of the times for each of the receive lines. A processor is configured to estimate velocity from the sparsely tracked displacements. A display is operable to display the velocity.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Sparse ARFI tracking at random locations with compressively sensed velocity estimation is provided. Displacements over a large imaging area are tracked by intelligently spreading the tracking locations in a sparse manner. A lower number of simultaneous receive beams and potentially fewer ARFI push transmissions may be needed using sparse sampling of displacement than full sampling.

When using just sparsely tracked data, conventional temporal peak displacement algorithms for estimating shear velocity perform poorly. There may not be enough samples of displacement over time for a given location to estimate the maximum displacement or shift in displacement profile accurately. With sparsely sampled displacements, a Radon transform shear velocity estimation may be used to find the velocity. Other slope calculations of receive line as a function of time may be used. Errors in velocity estimates may still result. To limit the errors caused by sparse sampling, the sparsely tracked data is combined with compressive sensing reconstruction. For ultrasound systems with a limited capability of simultaneous receive beams or for estimating velocity in multiple planes (e.g., azimuth and elevation sampling), multiple ARFI transmissions may be reduced or avoided for estimating velocity.

Figure 1:
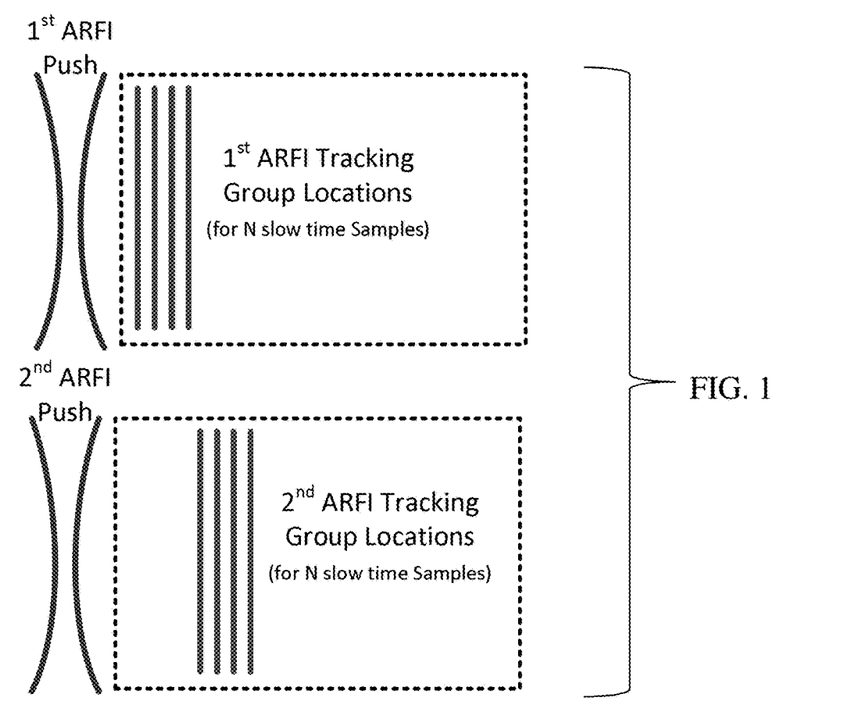
FIG. 1 illustrates an approach for fully sampling displacement by receive line and time.
Figure 2:
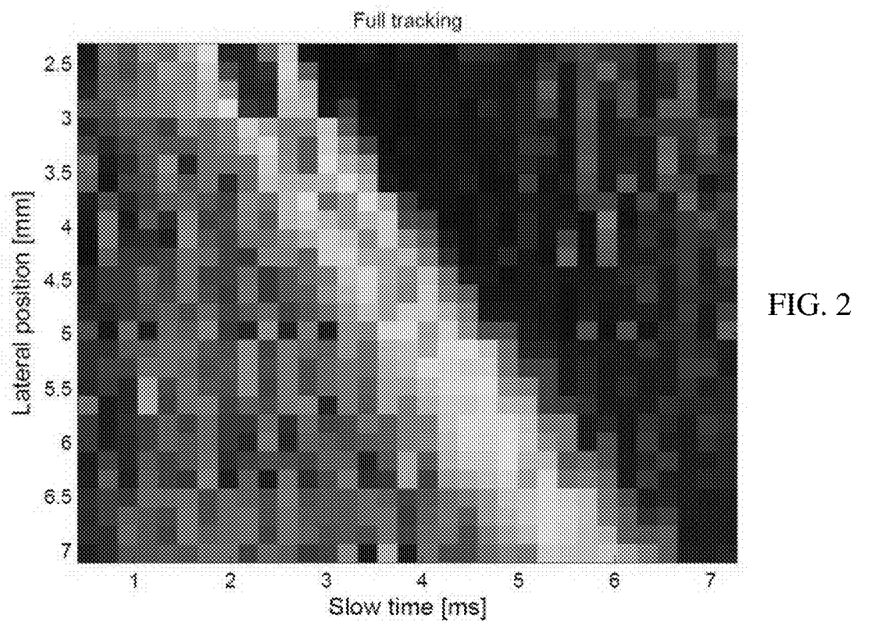
FIG. 2 is an example distribution of displacement by receive line and time for the full sampling of FIG. 1.

FIGS. 1 and 2 show displacement sampling in conventional ARFI imaging. Displacements estimated over a large region with a system that has a limited beamformation speed require repeated ARFI pushes. FIG. 1 shows a region of interest as the dashed box. Four simultaneous receive beams along the four receive lines are shown in the box. After transmission of an ARFI excitation pulse, multiple scans of the same four lines are performed to track displacement at the four locations over time. For the temporal scanning, the same group of receive lines are scanned over a period, such as over 7 ms. With each ARFI push, only a limited number of locations are tracked over N slow time samples. Given the region of interest of FIG. 1, seven repetitions of the ARFI excitation pulse and responsive displacement monitoring at respective seven different sets of receive lines are performed.

After all the echoes from the lateral locations within the desired region have been acquired, the raw data is passed through a displacement estimation process, providing a displacement for each of the times and locations. The result is a displacement profile for each receive line location over time. FIG. 2 shows a representation of the displacement information. The x-axis is the slow time or sample rate for displacement, and the y-axis is the lateral position or receive line. The brightness or color is the magnitude of the displacement. For a given receive line (e.g., receive line at 3 mm), a displacement over 7 ms is measured. In this example, about five displacements are measured sequentially over each millisecond. Since four simultaneous receive beams are used, the displacements over the slow time for four lateral positions are acquired at the same times. For other receive lines, the sequence of ARFI excitation pulse and tracking displacement over the 7 ms is repeated.

In the conventional approach, the maximum displacement over time is found for each lateral position. Given the distance from the ARFI focus and the time of the maximum displacement caused by the wave, a velocity of the wave traveling to that location is calculated. A velocity is determined for each location. The velocities may be displayed as spatial information or combined (e.g., averaged) to represent a velocity in that area. In the representation of FIG. 2, the slope of the line (e.g., high displacement ridge) is directly proportional to the shear velocity estimate. This maximum displacement process, while direct, may require multiple tracking locations and consequently many ARFI pushes as represented in FIG. 1. The result is an increased risk of transducer and patient temperature, more cooling time between ARFI excitation pulses, and longer estimation process due to the cooling time and/or full sampling of displacement.

Figure 3:
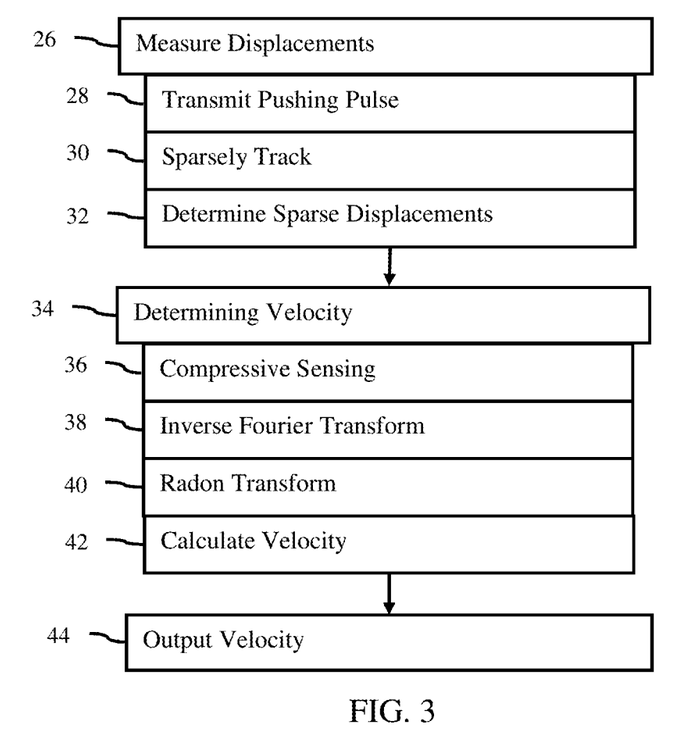
FIG. 3 is a flow chart diagram of one embodiment of a method for sparse tracking in acoustic radiation force impulse imaging.

FIG. 3 shows one embodiment of a method for sparse tracking in acoustic radiation force impulse imaging. Rather than fully sampling displacement in location and time, sparse sampling in location and/or time is used. Using Radon transform, line fitting and slope calculation, or other process, the velocity is estimated from the sparsely sampled displacements.

Figure 16:
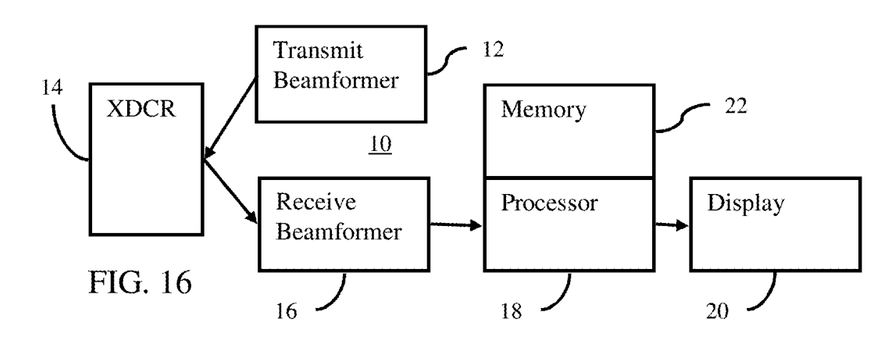
FIG. 16 is one embodiment of a system for acquisition control for sparse tracking in acoustic radiation force impulse imaging.

The method is implemented by the system of FIG. 16 or a different system. For example, any now known or later developed ultrasound scanner performs act 26. A processor, controller, or image processor of the ultrasound scanner performs acts 34 and 44. Alternatively, a processor of a computer or workstation separate or remote from the ultrasound scanner performs acts 34 and 44. Transmit beamformers, memory, detectors and/or other devices may be used to acquire the data, perform one or more of the acts, and/or output the data. The processor may control the devices to perform the method of FIG. 3.

The acts described below are for shear wave velocity estimation. Shear waves travel laterally, so lateral estimates at a given depth or depth range are used. In other embodiments, the velocity of a longitudinal or other wave is estimated. The displacement sampling may be spatially sparse in depth rather than or in addition to lateral directions. Any of elasticity, shear wave, or other ARFI induced wave characteristic estimation may use the sparse displacement sampling of the method. Velocity is used herein as the characteristic, but other characteristics parameterizing the tissue response to the acoustically induced wave may be estimated.

Additional, different, or fewer acts may be provided. For example, the method is performed without outputting velocity in act 44. As another example, acts 36-42 represent one example sequence for determining the velocity of act 34. Other acts or sub-sets may be used to determine the velocity from sparse displacement sampling. For example, Radon transform of act 40 is provided without the compressive sensing of act 36 and the inverse Fourier transform of act 38. As another example, act 42 is performed by line fitting and slope calculation without any of acts 36-40. In other examples, filtering or other data processing is applied to the displacements.

The acts are performed in the order described or shown, but may be performed in other orders. For example, act 28 shows transmission of a single excitation pulse. Act 28, and the responsive acts 30 and 32, may be repeated to measure the sparse distribution more densely for a region of interest or for a larger region of interest. This repetition occurs before the determination of act 34.

In act 26, the ultrasound scanner measures echoes for displacements in response to a single excitation pulse. The measures for more locations than a simultaneous receive beamform capability of the ultrasound scanner are measured in response to the single excitation pulse by sparsely sampling the displacements. By using sparse displacement measurement, displacements over a larger lateral region or more lateral locations may be measured in response to a single excitation pulse than if full temporal sampling of displacement is used. The region may be further expanded by repeating measurement in response to one or more other excitation pulses.

Figure 4:
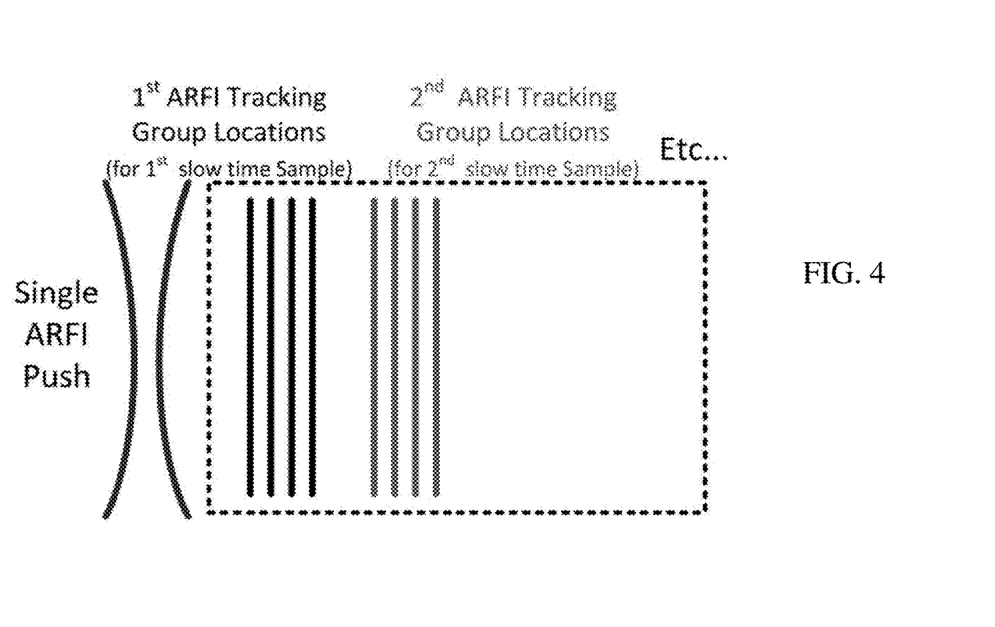
FIG. 4 illustrates an example approach for sparsely sampling displacement by receive line and time.

The displacements are measured by performing acts 28-32. In act 28, an ARFI push is transmitted by the ultrasound scanner into tissue of a patient. The transmission is a transmit beam focused at a depth or range of depths. The ARFI transmit beam is transmitted along a transmit scan line. The focal depth is on the transmit scan line. FIG. 4 shows the ARFI transmission as an excitation pulse with a beam width representation. The narrow portion is the focal region.

An array of elements in an ultrasound transducer transmits the ARFI beam converted from electrical waveforms. The acoustic energy is transmitted to the tissue in a patient. The acoustic waveform is transmitted for generating a shear, longitudinal, or other wave as stress to displace tissue. The excitation is an ultrasound excitation pulse. The acoustic energy is focused to apply sufficient energy to cause generation of one or more waves travelling through the tissue from the focal location. The acoustic waveform may itself displace the tissue. Other sources of stress may be used.

The shear wave or waves are generated at the focal region and propagate laterally, axially, and/or in other directions from the focal region. The waves may travel in multiple directions. The waves reduce in amplitude as the waves travel through the tissue.

To generate the wave, high amplitude or power excitations are desired. For example, the excitation has a mechanical index of close to but not exceeding 1.9 at any of the focal locations and/or in the field of view. To be conservative and account for probe variation, mechanical index of 1.7 or other level may be used as the upper limit. Greater (e.g., MI exceeding 1.9) or lesser powers may be used.

The excitation pulse is transmitted with waveforms having any number of cycles. In one embodiment, one, most, or all of the waveforms for a transmit event have 100-2,000 cycles. The number of cycles is tens, hundreds, thousands, or more for the continuous transmit waveforms applied to the elements of the array for the excitation pulse. Unlike imaging pulses that are 1-5 cycles, the ARFI excitation pulse has a greater number of cycles to generate sufficient stress to cause the wave for displacing tissue with an amplitude sufficient to detect.

In act 30, the generated wave is tracked. The wave is generated in response to the ARFI transmission. The tissue response is a function of the wave created by the ARFI beam and the tissue characteristics. The wave is tracked at any locations. For a shear wave, the wave is tracked at laterally spaced locations of a same depth or depth range. The tracking detects the results of the wave rather than specifically identifying where the wave is located at a given time.

The tracking is performed by ultrasound scanning. B-mode or other scanning along one or more receive lines is performed to track. The displacement indicates the wave, such as no displacement indicating an absence of the wave and a displacement indicating tissue effect caused by the wave. As the wave passes a given location, the tissue displaces by an amount or distance that increases to a peak amount and then decreases as the tissue returns to rest. The tracking may detect the effects of the wave at any stage (i.e., no wave, increasing displacement, maximum, or decreasing displacement).

The tissue is scanned multiple times to determine the displacement, such as scanning a region at least twice. To determine displacement at one time, a sample echo return is compared to a reference. The displacement is provided as the difference or offset from the reference scan (first scan) and a later scan (displacement measure). The tissue is scanned using any imaging modality capable of scanning for displacement during the tissue's response to the excitation waveform, such as during or after application of the ARFI excitation pulse.

For ultrasound scanning, the wave is detected at locations adjacent to and/or spaced from the focal region for the ARFI excitation pulse. FIG. 4 shows the region for tracking as the dashed region. The displacements are sampled at various receive lines, eight of which are represented as parallel vertical lines. Non-parallel and/or non-vertical receive lines may be used. Any number of lateral locations may be used, such as twenty-eight.

To detect the displacement, ultrasound energy is transmitted to the tissue undergoing displacement, and reflections of the energy are received. To detect tissue response to waves in a region of interest, transmissions are made to the region, and detection is performed in the region. These other transmissions are for detecting the waves or displacement rather than causing the wave or displacement. The transmissions for detection may have lower power and/or short pulses (e.g., 1-5 carrier cycles).

The transmissions for detection may have a wider beam profile along at least one dimension, such as laterally, for simultaneously forming receive samples along a plurality of scan lines (e.g., receive beamforming simultaneously along four or more receive lines). Receive beamformers have limited capabilities for simultaneous receive beamformation, such as a multiple of two or more. For example, only four or fewer simultaneous receive beams may be formed for tracking. FIG. 4 shows two sets of such receive lines. The tracking transmissions and corresponding receive beams are performed sequentially to the two different sets of locations shown in FIG. 4 and possibly other locations. Some beamformers may be only capable of two or one receive beam per transmit beam in tracking. For a given receive event (i.e., receiving echoes responsive to a given transmission for tracking), N receive beams are formed.

A region of interest is monitored to detect the wave. The region of interest is any size. For example, the wave is detected along various depths of one or more lines in ARFI imaging. As another example, the displacements are tracked at each of a plurality of laterally spaced locations for a limited depth in shear wave imaging.

In full sampling, the transmission and reception for detection or tracking are performed multiple times for each receive line to determine change due to displacement over time. Any transmission and reception sequence may be used. For sparse sampling, the number of scans for a given scan line or set of simultaneously received beams is limited in time and/or space. For example, a reference scan of all of the receive lines in the region of interest is performed prior to the ARFI transmission of act 28. After the ARFI transmission of act 28, N different tracking groups or sets of simultaneous receive lines are used. N is a multiple of two or more of the number of simultaneous receive beams for which the receive beamformer is capable. In the example of FIG. 4, the receive beamformer is capable of four simultaneous receive beams. The region of interest, at a desired resolution, provides for eight or more laterally spaced locations for tracking, such as tracking at 28 receive lines. The tracking or receive operation occurs for more than four of the receive lines in response to a given ARFI transmission. As a result, the temporal sampling for displacement at a given location is less since at least one transmit and receive event for tracking occurs at another location not in the beam group or number of beam capability of the receive beamformer. By tracking for all or a sub-set of lateral locations greater than a simultaneous capability of the beamformer, the resulting samples for displacement calculation are sparse in time and/or location. Each location is sampled fewer times. For example, each location is sampled just once other than a reference. In other examples, each location is sampled two or more times but fewer than half, fewer than ¾, fewer than ¼, or other rate of the number of tracking transmit/receive events possible over the slow time period (e.g., over 7 ms).

Sparse tracking speeds up the process by gathering information for more locations than could be monitored by a given beamformer with full sampling. More or the entire region of interest is monitored at the same density of sample locations but less temporal resolution at each location. For example, the receive beamformer is capable of N simultaneous receive beams (e.g., 4). The acoustic echoes for N displacements are measured per receive event for N tracking lines. This measurement is repeated for other groups of N tracking lines rather than for the same group of tracking lines, at least for one or more times during the passing of the wave generated in response to a given ARFI transmit. XN receive lines are measured in response to a single excitation pulse, where X is two or more. Rather than just measure the same N lines in response to a excitation pulse, all or XN lines are measured, resulting in fewer samples for each lateral location. Acoustic return for measuring displacements are not measured for at least some of the receive lines at the full sampling, at more than half the full sampling, or even more than once during passing of the shear wave. Depending on the sampling pattern, there may be no measures of displacement performed during passing of the wave for one or more of the locations.

Any sampling pattern providing the sparse measurements may be used. For example, the lateral locations are measured in groups of N from left to right or vise versa. FIG. 4 shows one sample for each of two different groups of N lines (e.g., 4 simultaneous receive beams). Rather than repeating sampling along the same lines for each ARFI excitation pulse, the sampling is along different receive lines over time for a given ARFI excitation pulse. This pattern may be repeated if there is sufficient time. Alternatively, each group of N lateral locations is measured more than once before moving to the next group. More complex patterns may be used, such as measuring along some lines or lateral locations more frequently (e.g., closer to the ARFI focus) and/or measuring based on the expected propagation of the wave.

In one embodiment, the scan pattern of the receive lines or lateral locations is random. The slow-time samples are randomly placed along the receive lines in the region of interest. The displacements are measured at random locations over time. The tracking with the receive beams is randomly distributed along the tracking lines.

The random placement is of N groups of adjacent receive lines. Alternatively, each lateral location is randomly sampled without N grouping, such as simultaneously receiving echoes along N lines that may or may not be adjacent due to the random placement and repeating along other randomly assigned lines. The random assignment may be created on the fly or while the scanning occurs. Alternatively, the random assignment is performed once and used for each implementation. Pre-determined randomly assigned sampling is used. In alternative embodiments, non-random assignment is used.

The random assignment for sparse sampling of the displacements speeds up the estimate of velocity due to being sparse. The randomness may better provide for velocity estimation using Radon transformation or other angle-based estimate. The tracking lateral locations are assigned in a random way for tracking from a single ARFI push (i.e. all the slow time 'samples' during a single push are distributed laterally in a pseudo random way).

Figure 5:
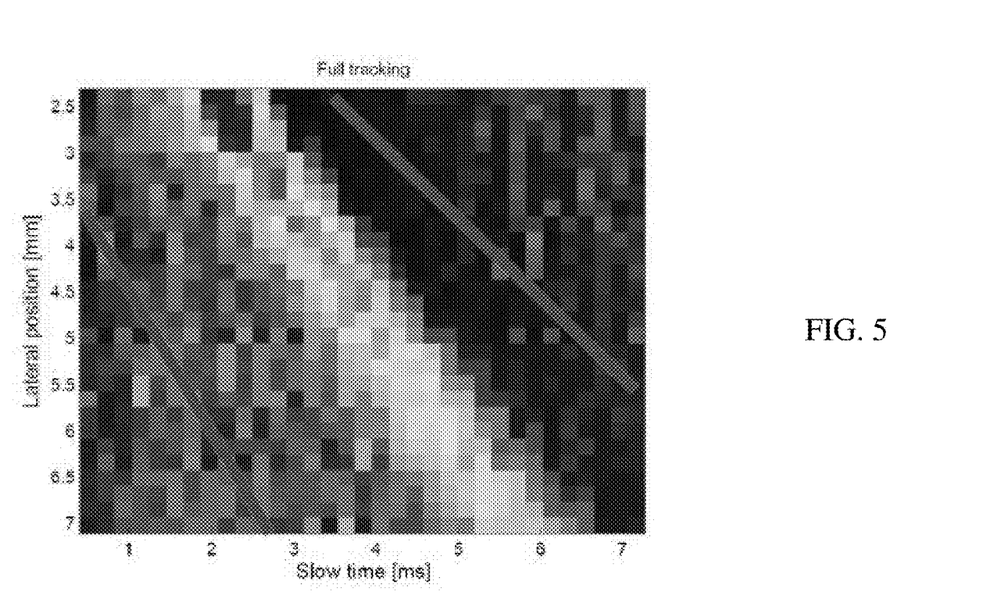
FIG. 5 illustrates a region of the receive line and time space for limiting random, sparse sampling.

For either random or patterned sampling, the lateral locations sampled at any given time may be limited. For example, pseudo-random sampling is provided. The tracking beam locations for each slow time are randomly under sampled using a uniform distribution but are also constrained to lie within a potential shear velocity "cone." The shear velocity that may exist in soft tissues or a range of different tissues is limited. The cone is defined by the minimum and maximum possible shear velocities. The sampling is limited to be within this range of velocities. The velocity maps to the distance of a lateral location relative to the time from the generation of the shear wave by the ARFI. FIG. 5 shows a cone (e.g., two red lines) representing the minimum time to reach each location and the maximum time to reach each location. This cone is represented on the full sampling of FIG. 2, but is applicable to sparse sampling. The sampling is limited to be within this cone of likely shear. Any displacement outside of the cone is likely noise rather than due to shear. The tracking scans occur over a range of times where the desired waveform (e.g., shear wave) may be passing through the tissue.

The cone may be defined based on likely human tissues. Alternatively, the cone is based on an application. For example, a liver application may provide for a different range or cone than a muscle application since shear travels in the different tissues and/or types of lesions found in those tissues at different rates. Given a tissue or application, the range of locations as a function of time at which the wave would be passing is set.

Figure 6:
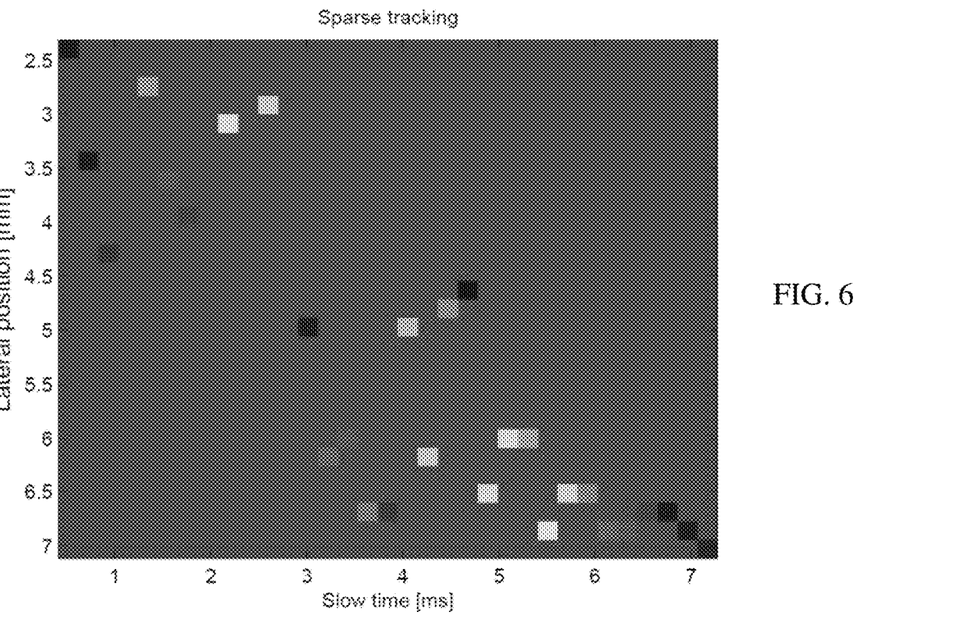
FIG. 6 is an example distribution of sparsely sampling for displacement by receive line and time.

FIG. 6 shows results of random sampling with a receive beamformer capable of only one receive beam at a time. The sampling is restricted by the cone of possibility, but is otherwise random within those limits. The random format may be selected as one that is more uniformly distributed than other random formats. For each sample time after a single ARFI push, only one lateral location is sampled due to a one beam per event limitation of the beamformer or use of the beamformer with one beam per event. For the lateral locations from 2.5 to 7 mm from the ARFI focus, any number of samples may be provided due to the randomness. In the example of FIG. 6, most of the lateral locations are sampled at only one time. Some are sampled at two times (e.g., 5 mm and 6.16 mm), some at three times (e.g., 6 mm and 6.6 mm), some at four times (e.g., 6.66 mm and 6.82 mm), and some not sampled at all (e.g., 2.66 mm and 4.5 mm). The increasing number of samples for further away lateral locations is due to the cone or diverging shape of the limitation making the further locations available for sampling over a greater range of times.

Comparing FIG. 2 with FIG. 6, there are many fewer samples acquired for the sparse sampling of FIG. 6. In FIG. 2, there are 28 lateral locations each fully sampled 33 times over the 7 ms, providing 924 samples of the receive echoes in tracking. For the sparse sampling of FIG. 6, there are 33 samples, one for each time. In other embodiments, there may be more or fewer samples. For example, by performing parallel receive beamforming with four simultaneous beams, there may be 132 samples with four samples for each time. 132 is still well short of the 924 samples and still allows tracking over the larger area in response to one ARFI excitation pulse rather than seven.

FIG. 6 shows sampling in two dimensions, lateral position (e.g., azimuth) and time. In other embodiments, sampling is provided over additional dimensions. For example, the tracking lines are distributed in both azimuth and elevation relative to the transducer. As another example, the process is repeated at different depths as well, providing four dimensional tracking (e.g., azimuth, elevation, depth, and time).

Returning to FIG. 3, the samples are used to determine displacement in act 32. The displacement at each of the locations for any time for which an echo was sampled is determined. For the shear wave imaging, the displacement at the depth or depth range along each tracking line is determined.

The displacement is calculated from the ultrasound scan data. The tissue moves between two scans. A reference scan is performed before the ARFI transmit of act 28 and/or after the generated wave has passed the location. The data of the sample scan or the reference scan is translated or shifted in one, two, or three dimensions relative to the data in the other scan. For each possible relative position, an amount of similarity is calculated for data around a location. The amount of similarity is determined with correlation, such as a cross-correlation. A minimum sum of absolute differences or other function may be used. The spatial offset with the highest or sufficient correlation indicates the amount of displacement for a given location. In other embodiments, a phase offset of data received from different times is calculated. The phase offset indicates the amount of displacement. In yet other embodiments, data representing a line (e.g., axial) at different times is correlated to determine a shift for each of a plurality of depths along the line.

A single ARFI excitation pulse is used to estimate displacements for all the locations. FIG. 6 shows estimation of all locations in a 2.5-7 mm region of interest at a given depth. The excitation pulse and tracking may be repeated for different depths. To monitor a larger lateral region, excitation pulses and tracking are repeated for other locations.

FIG. 6 shows the displacements as color for the various locations and times. The blue background represents locations and times without any sample, so no corresponding displacement. The other locations' color indicates an amount of displacement. Due to the timing of the sampling not being specifically for unknown time of maximum displacement, the sampled displacements may or may not be associated with a maximum displacement caused by the wave passing the tissue. Due to the sparse sampling, a complete, ¾, or even half resolution profile of displacement as a function of time is not provided for any of the locations. In FIG. 6, the sparse displacements are provided as one for each receive beam with N displacements per receive event (i.e., in FIG. 6, N=1). Since the profile of displacement as a function of time for each location has low resolution (e.g., 0-4 samples in the example of FIG. 4), using the displacement profile over time to calculate the velocity for that location is unreliable.

In act 34 of FIG. 3, the velocity of the wave generated by the single or a few excitation pulses is determined. The velocity is determined from the displacements. The velocity is to be determined without identification of the maximum displacement at any given location. The magnitudes of the displacements are determined without specifically (e.g., without a processor calculating) identifying a time of maximum displacement for any of the tracking lines or corresponding lateral locations. Estimations of velocity with the under sampled displacements is not performed with conventional temporal-peak estimation methods, but instead uses a transform method.

Figure 7:
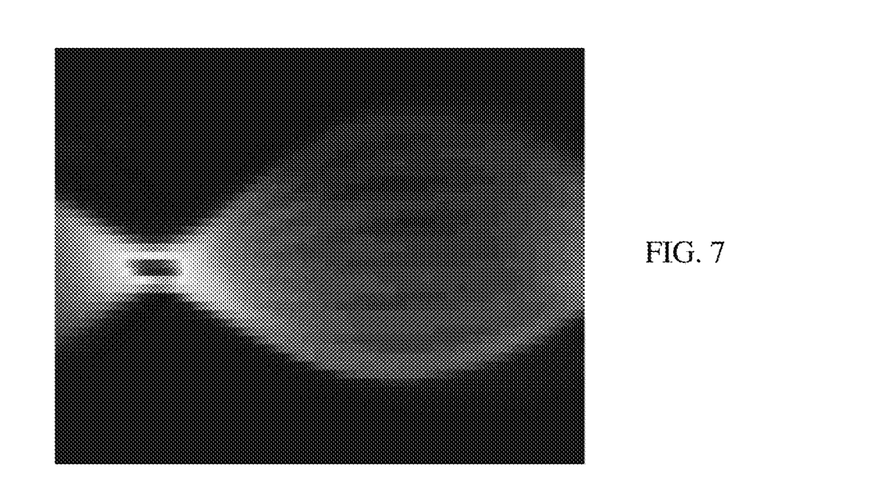
FIG. 7 shows an example Radon transform of FIG. 2.
Figure 8:
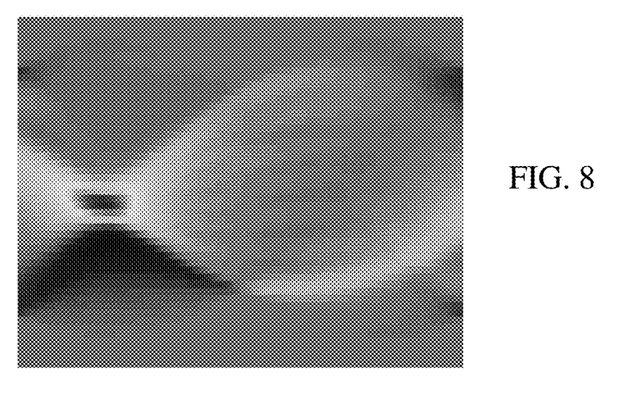
FIG. 8 shows an example Radon transform of FIG. 6.

In one embodiment, the transform is a Radon transform. The Radon transform is applied to the displacement data, such as represented in FIG. 6. The Radon transform projects the data along lines at different angles. The projection angle with the highest intensity along the angle indicates the wave. FIG. 7 shows a Radon transform sinogram of the full sampling of FIG. 2. FIG. 8 shows the Radon transform sinogram of the sparse sampling of FIG. 6. The x-axis is the projection angle. For projection, a sum of the displacements orthogonal to the angle is performed, resulting in a line of displacement magnitudes along the projection angle. The y-axis is the projected or summed displacement along the orthogonal. Each x-axis vertical line represents the series projection of displacements orthogonal to that angle. The velocity is determined from the angle. The angle represents a distance as a function of time of the wave. Other transforms may be used.

In other embodiments, a line fitting is used (e.g., least squares). A straight line is fit to the displacements as a function of time, such as fitting the line to FIG. 6. The fitting may be weighted by the magnitudes of the displacements. The displacement magnitudes may be adjusted to account for wave attenuation as a function of distance before the displacement weighted fitting. Once fit, the line provides a slope or angle used to calculate the velocity.

As shown in both FIGS. 7 and 8, while the projection images are qualitatively similar, the peak intensity angle estimate in the under sampled image of FIG. 8 may be prone to more noise as the reduced number of samples tends to spread out the projection peak and decrease the overall displacement signal-to-noise ratio (SNR) from lowered signal levels. To reduce these concerns, the displacements may be filtered or otherwise processed. FIG. 3 shows one example approach to reduce errors due to under sampling. Acts 36 and 38 are performed prior to performing the Radon transform in act 40 and calculating the velocity in act 42. Additional, different, or fewer acts may be used. For example, acts 40 and 42 are performed without acts 36 and 38. As another example, act 42 is performed without act 40.

In act 36, compressive sensing is performed on the sparsely sampled displacements. The data represented in FIG. 6 or other sparse sampling of displacements is subjected to compressive sensing. In order improve the SNR of the shear velocity estimates from the under sampled displacements, a compressed sensing approach is used where Fourier sparsity of the slow-time displacements is assumed.

Any compressed sensing signal recovery may be used. In one embodiment, orthogonal matching pursuit is used. Orthogonal matching pursuit is a greedy-type recovery algorithm that only recovers the most significant Fourier coefficients from the under sampled spectrum. The number of coefficients to recover is predetermined or user selected. The sparse displacement sampling is compressively sensed to reconstruct a Fourier spectrum.

Figure 9:
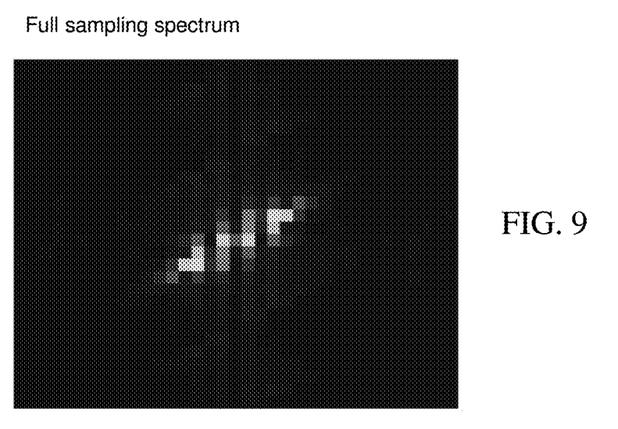
FIG. 9 shows an example two-dimensional Fourier spectrum of the full sampling of FIG. 2.
Figure 10:
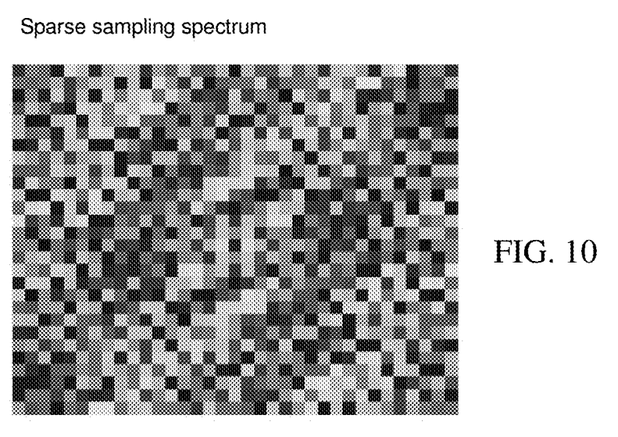
FIG. 10 shows an example two-dimensional Fourier spectrum of the sparse sampling of FIG. 4.
Figure 11:
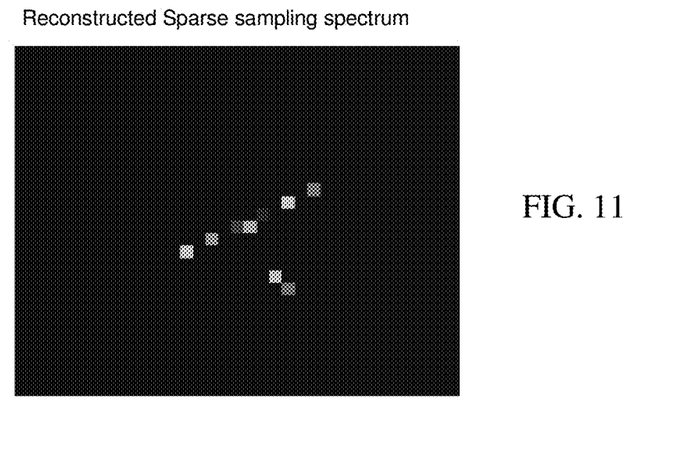
FIG. 11 is an example two-dimensional reconstructed Fourier spectrum from the sparse sampling of FIG. 4 using compressive sensing.

An example of compressive sensing is explained with reference to FIGS. 9-11. FIG. 9 shows a two-dimensional Fourier spectrum of the fully sampled displacements as a function of time of FIG. 2. FIG. 10 shows the two-dimensional Fourier spectrum of the sparsely sampled displacements of FIG. 6. By using compressive sensing of the sparsely sampled displacements of FIG. 6, the Fourier spectrum of FIG. 11 results. FIG. 11 is a two-dimensional Fourier spectrum reconstructed using compressive sensing. Much of the noise from the sparse sampling is reduced or removed (compare FIGS. 10 and 11).

Figure 12:
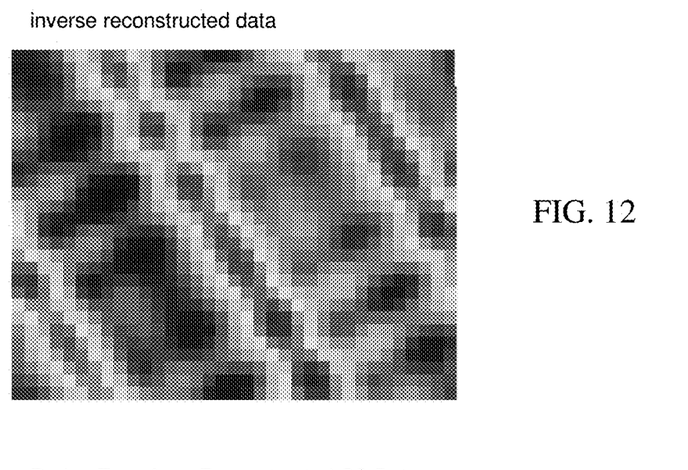
FIG. 12 is an example inverse Fourier transform of FIG. 11.

In act 38, the reconstructed Fourier spectrum is inverse Fourier transformed. The results or output of the compressive sensing are transformed from the frequency domain into the location as a function of slow-time domain. For example, FIG. 12 shows an example inverse Fourier transform of the Fourier spectrum of FIG. 11. The result has three high magnitude ridges in parallel. Three instead of one ridge is the result of discontinuities in the 2D Fourier Spectrum, but the Radon transform, line fitting, or other wave detection may still operate. In other examples, only one or other number of ridges occur. The spectrum may be smoothed prior to the inverse Fourier transform to provide a single ridge.

Figure 13:
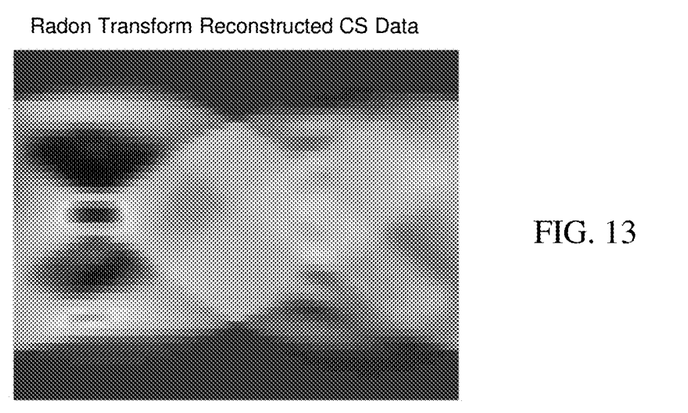
FIG. 13 is an example Radon transform of FIG. 12.

In act 40, the Radon transform is applied to the output or results of the inverse Fourier transform. FIG. 13 shows the Radon transform sinogram. As compared with FIG. 8, the intensity is more focused. The effects of noise from the sparse sampling of the displacements are reduced. Other transforms or angle identification approaches may be used.

In act 42, the velocity is calculated from the results or output of the Radon transform. The angle with the maximum intensity in the Radon transform sinogram is identified. The angle indicates the tracking line or lateral location as a function of time. The slope of this angle is proportional to the velocity. The slope itself is used as the velocity, or the velocity is calculated from the slope.

Figure 14:
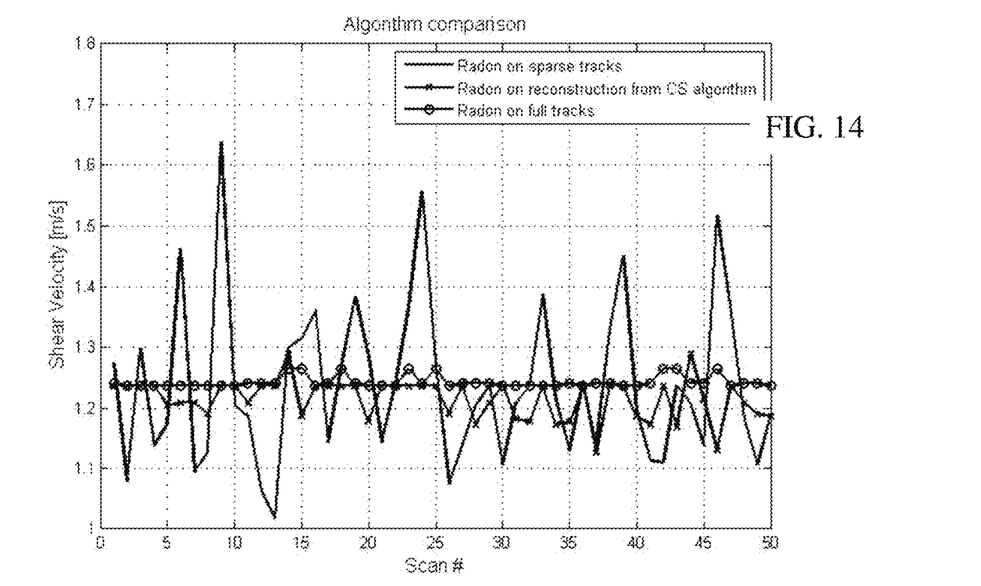
FIG. 14 is a graph of shear velocity as a function of a number of scans or over time using Radon transform on sparse displacements without compressive sensing, on sparse displacements with compressive sensing and on fully sampled displacements.

FIG. 14 shows a comparison of shear velocity calculation based on a Radon transform of the fully sampled displacements, based on a Radon transform of the sparsely sampled displacements without compressive sensing, and based on a Radon transform of the sparsely sampled displacements with compressive sensing. The velocities of the full tracking have the least variance. The scan number of the x-axis is for different data sets from different locations of the phantom in order to show variability. The shear velocity from the Radon transform of sparse displacements without compressive sensing has the greatest variance. The compressive sensing reduces the variance in the estimated shear velocity. In the example of FIG. 14, the velocity from the full sampling has a mean of 1.2495 m/s with a standard deviation of 0.0306. The velocity from sparse sampling without compressive sensing has a mean of 1.2228 m/s with a standard deviation of 0.1903. The velocity from sparse sampling with compressive sensing has a mean of 1.2059 m/s with a standard deviation of 0.0814. Compressive sensing reduces the variance of the estimates.

Other characteristics than velocity may be calculated and/or the velocity may be used to calculate a further characteristic. For example, a shear modulus or other elasticity characteristic is calculated.

Figure 15:
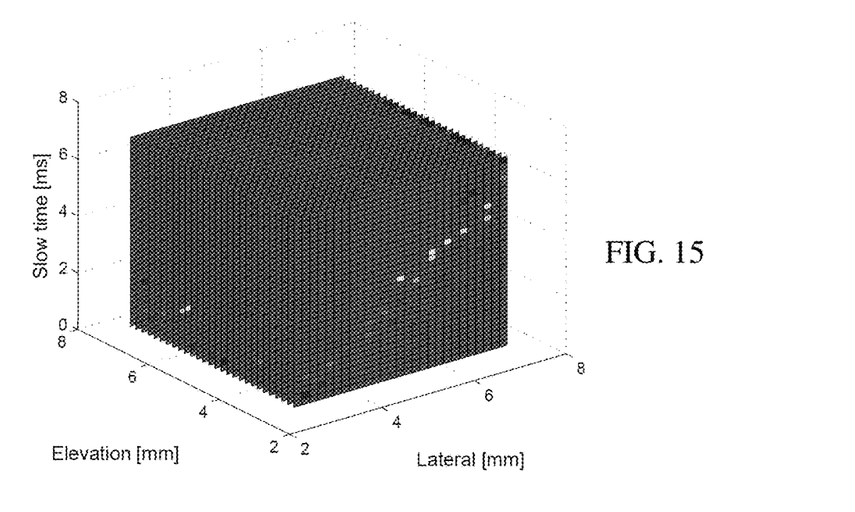
FIG. 15 is an example sparse displacement sampling in three-dimensions.

The velocity may be calculated from samples along different lateral locations in a line, such as azimuth spaced locations at a depth. In other embodiments, the displacements are sampled at lateral locations in both azimuth and elevation at a depth. FIG. 15 shows a volume formed from sample locations in two spatial dimensions (e.g., azimuth and elevation relative to the transducer) and in time (e.g., slow time). Tracking lines are spaced in azimuth and elevation. The tracking lines are randomly sampled, or other sparse sampling approach is applied. FIG. 15 represents no displacement sample as the background blue level and the sparsely obtained displacement samples as other colors.

The added dimension of tracking distribution may result in a much greater number of tracking lines. As a result, a given beamformer may be less able to fully sample without ARFI repetition, transducer heating, and/or patient heating. Even receive beamformers that may simultaneously form tens of receive beams (e.g., 32 or 64 simultaneous receive beams) may not be able to fully sample. For sampling a large volume, sparse sampling and corresponding velocity estimation may be used. As compared to full sampling, the sparse sampling may reduce collection times while still providing good estimates of shear velocity.

In act 44 of FIG. 3, the velocity is output. The output is to a memory, over a network, or on a display. For display, the velocity or other characteristic of the wave is displayed as a value in numbers and/or letters (e.g., "2.0 m/s"). Alternatively, a graphic representation of the velocity or characteristic is used, such as a pointer on a scale or a bar graph. The velocity may be displayed as a color or other indexed symbol.

In one embodiment, a single velocity is determined. A user positions a pointer on an image. In response, the ultrasound scanner outputs a velocity calculated for that point (e.g., the point is used for the ARFI focus and the velocity for a small region next to or around the point is calculated). In other embodiments, more than one velocity is output. The velocity at different locations is found. For example, a curve is fit, and the slope of the curve at different locations represents the different velocities. As another example, different measurements are made for different locations.

An image of the velocity is a display of a single velocity or a display of multiple velocities. For velocities measured at different locations, the image may include a one, two, or three-dimensional representation of the velocity or characteristic as a function of space or location. For example, the shear velocity throughout a region is displayed. Shear velocity values modulate color for pixels in a region in a grayscale modulated B-mode image. The image may represent displacement information, such as shear or moduli (e.g., the shear moduli) for different locations. The display grid may be different from the scan grid and/or grid for which displacements are calculated. Color, brightness, luminance, hue, or other characteristic of pixels is modulated as a function of the information derived from the displacements.

FIG. 16 shows one embodiment of a system 10 for sparse tracking in acoustic radiation force impulse imaging. Ultrasound generates tissue displacement, such as through creation of a shear or longitudinal wave, and scan data responsive to the tissue responding to the displacement is used to determine velocity or other characteristic of the wave in the tissue. To speed the scanning and/or reduce heating, the tissue response may be sampled sparsely. More (e.g., by a factor of 2, 3, 4, 5, or more) laterally spaced locations than there are simultaneous receive beams are sampled in response to a given ARFI excitation pulse.

The system 10 is a medical diagnostic ultrasound imaging system. In alternative embodiments, the system 10 is a personal computer, workstation, PACS station, or other arrangement at a same location or distributed over a network for real-time or post acquisition imaging.

The system 10 implements the method of FIG. 3 or other methods. The system 10 includes a transmit beamformer 12, a transducer 14, a receive beamformer 16, an image processor 18, a display 20, and a memory 22. Additional, different or fewer components may be provided. For example, a user input is provided for manual or assisted designation of a region of interest for which information is to be obtained.

The transmit beamformer 12 is an ultrasound transmitter, memory, pulser, analog circuit, digital circuit, or combinations thereof. The transmit beamformer 12 is configured to generate waveforms for a plurality of channels with different or relative amplitudes, delays, and/or phasing. The waveforms are generated and applied to an array of the transducer 14 with any timing or pulse repetition frequency. For example, the transmit beamformer 12 generates a excitation pulse for calculating velocity in a region of interest and generates corresponding transmissions for tracking resulting displacements with ultrasound.

The transmit beamformer 12 connects with the transducer 14, such as through a transmit/receive switch. Upon transmission of acoustic waves from the transducer 14 in response to the generated waves, one or more beams are formed during a given transmit event. The beams are excitation pulses and/or tracking beams. For scanning tissue displacement, a sequence of transmit beams are generated to scan a one, two or three-dimensional region. Sector, Vector®, linear, or other scan formats may be used. The scanning by the transmit beamformer 12 occurs after transmission of the excitation pulse, but may include scanning for reference frames used in tracking before transmitting the excitation pulse. The same elements of the transducer 14 are used for both scanning and displacing tissue, but different elements, transducers, and/or beamformers may be used. Any pattern may be used for scanning lines in tracking, such as a random pattern matched to the random receive sampling.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. For example, the transducer 14 is a one-dimensional PZT array with about 64-256 elements.

The transducer 14 connects with the transmit beamformer 12 for converting electrical waveforms into acoustic waveforms, and connects with the receive beamformer 16 for converting acoustic echoes into electrical signals. The transducer 14 transmits the excitation pulse and tracking beams. The waveforms are focused at a tissue region or location of interest in the patient. The acoustic waveforms are generated in response to applying the electrical waveforms to the transducer elements. For scanning with ultrasound to detect displacement, the transducer 14 transmits acoustic energy and receives echoes. The receive signals are generated in response to ultrasound energy (echoes) impinging on the elements of the transducer 14.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission for detection. Dynamic focusing on receive may be provided. Where only one depth or depth range is of interest, dynamic focusing may or may not be provided. The receive beamformer 16 outputs data representing spatial locations using the received acoustic signals. Relative delays and/or phasing and summation of signals from different elements provide beamformation. In alternative embodiments, the receive beamformer 16 is a processor for generating samples using Fourier or other transforms.

For parallel receive beamformation, the receive beamformer 16 is configured to include one or more additional sets of channels and corresponding summer or summers. Each channel applies relative delays and/or phasing to from a beam with the summer. The receive beamformer 16 may have any number N of sets of channels and summers, such as N=1-8, for forming a corresponding number of beams simultaneously or in response to a same tracking transmit beam.

The receive beamformer 16 may include a filter, such as a filter for isolating information at a second harmonic or other frequency band relative to the transmit frequency band. Such information may more likely include desired tissue, contrast agent, and/or flow information.

The receive beamformer 16 outputs beam summed data representing spatial locations. Data for a single location, locations along a line, locations for an area, or locations for a volume are output. The data may be for different purposes. For example, different scans are performed for B-mode or tissue detection than for shear or longitudinal wave detection. Alternatively, the B-mode data is also used to determine displacement caused by a shear or longitudinal wave.

The receive beamformer 16 is configured to sparsely track displacements responsive to a excitation pulse. The echoes received by the transducer 14 are beamformed into data samples. These samples may be used for estimating displacements. The receive beamformer 16 is configured to sparsely track by forming receive beams for a sparse sampling in time and/or location to estimate displacements at those times and/or locations. The sparsely tracked measurements for displacements are distributed by receive line over sample time such that no displacements are provided for more than half of the sample times for each of the receive lines in response to a given excitation pulse. Rather than full sampling over a same length of time at each location, less than half, such as only 1-25% of the locations are samples at a given time. Where parallel receive beamforming is used, the receive beamformer 16 is configured to measure N of the displacements at each of the sample times with the receive lines for the displacements being randomly positioned over XN of the receive lines, where X is two or greater.

The processor 18 or a separate beamformer controller configures the beamformers 12, 16. By loading values into registers or a table used for operation, the values of acquisition parameters used by the beamformers 12, 16 for ARFI imaging are set. Any control structure or format may be used to establish the ARFI imaging sequence. The beamformers 12, 16 are caused to acquire data for ARFI imaging at a frame rate and/or with a resolution. Different values of one or more acquisition parameters may result in a different frame rate and/or resolution.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof or other now known or later developed device for detecting and processing information from beamformed ultrasound samples.

In one embodiment, the processor 18 includes one or more detectors and a separate processor. The separate processor is a control processor, general processor, digital signal processor, graphics processing unit, application specific integrated circuit, field programmable gate array, network, server, group of processors, data path, combinations thereof or other now known or later developed device for determining displacement and/or calculating velocity from displacements. The processor 18 is configured by software and/or hardware to perform the acts.

In one embodiment for ARFI imaging, the processor 18 estimates tissue displacement for each lateral location at none, one, or more times in correspondence with the sparse sampling. The data output by the receive beamformer 16 is used to determine the displacement at different times for different locations, but sparsely. The displacements are estimated for different locations at different times relative to the ARFI excitation pulse rather than each location at each time. The displacements may be obtained by correlating or otherwise determining level of similarity between reference data and data obtained to represent the tissue at a time.

The processor 18 is configured to calculate tissue characteristics form the displacements of the tissue at different locations over time. For example, a shear velocity is calculated from the displacements. In another example, the processor 18 calculates viscosity and/or modulus. The processor 18 may calculate other properties, such as strain or elasticity.

The processor 18 is configured to estimate the velocity or other characteristic from the sparse sampling of the displacements. For example, a slope of a line of detected displacements as a function of time is found. A line fitting may be used. In one embodiment, a Radon transform is used. The slope provides the distance as a function of time, yielding the velocity. The processor 18 may be configured to reduce noise in the velocity estimate caused by the sparse sampling. For example, the processor 18 performs compressive sensing on the sparse displacements, inverse Fourier transforms the output of the compressive sensing, applies the Radon transform to the output of the inverse Fourier transform, and then estimates the velocity from the angle of maximum in the Radon transform sinogram. The processor 18 may estimate the velocity in response to a single excitation pulse that has more lateral locations than the receive beamformer 16 is capable of scanning simultaneously. For example, the region may have more locations by a factor of 2, 3, 4, 5, or more than the number of simultaneous receive beams where the locations are sampled in response to one excitation pulse. In other embodiments, the sparse sampling and estimation of velocity are performed using multiple excitation pulses, but with sparse sampling.

The processor 18 generates and outputs image or display values mapped from the property to the display 20. For example, the velocity, shear modulus or other value is determined. A text or numerical indication of the property is displayed to the user. A graph of the property over time may be displayed.

In one embodiment, the property is displayed as a function of location. Values, graphs, and/or tissue representations may be displayed using the velocity at different locations. For a representation of the tissue, the magnitude of the tissue characteristic modulates the color, hue, brightness, and/or other display characteristic for different pixels representing a tissue region. The processor 18 determines a pixel value (e.g., RGB) or a scalar value converted to a pixel value. The image is generated as the scalar or pixel values. The image may be output to a video processor, look-up table, color map, or directly to the display 20.

The display 20 is a CRT, LCD, monitor, plasma, projector, printer or other device for displaying an image or sequence of images. Any now known or later developed display 20 may be used. The display 20 is operable to display one image or a sequence of images. The display 20 displays two-dimensional images or three-dimensional representations. The display 20 displays one or more images representing the tissue characteristic or other information derived from displacements. As an example, a velocity associated with a location indicated on a two-dimensional image or three-dimensional B-mode representation is displayed. Alternatively or additionally, the image is a graph.

The processor 18, the receive beamformer 16, and the transmit beamformer 12 operate pursuant to instructions stored in the memory 22 or another memory. The instructions configure the system for performance of the acts of FIG. 3. The instructions configure the processor 18, the receive beamformer 16, and/or the transmit beamformer 12 for operation by being loaded into a controller, by causing loading of a table of values (e.g., elasticity imaging sequence), and/or by being executed. The transmit beamformer 12 is configured by the instructions to cause generation of a excitation beam and tracking beams. The receive beamformer 16 is configured by the instruction to acquire data for tracking. The processor 18 is configured to estimate displacements and determine the velocity from sparse displacements.

The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A non-transitory computer readable storage medium having stored therein data representing instructions executable by a programmed processor for sparse tracking in acoustic radiation force impulse imaging, the storage medium comprising instructions for:

measuring, by an ultrasound scanner, displacements responsive to a wave in tissue of a patient, the wave generated from a single excitation pulse, the displacements measured at random locations over time, the random locations being assigned randomly in a sparse sampling;

determining a velocity of the wave generated by the single excitation pulse from the displacements; and outputting an image of the velocity.

2. The non-transitory computer readable storage medium of claim 1 wherein measuring comprises measuring N displacements per receive event for N tracking lines, respectively, and repeating the measuring for other groups of N of the tracking lines.

3. The non-transitory computer readable storage medium of claim 2 wherein the random locations are within a region of the tracking lines, the region and time limited by a velocity range.

4. The non-transitory computer readable storage medium of claim 1 wherein the ultrasound scanner is operable to receive beamform only N receive beams along N receive lines simultaneously, where N is an integer greater than 1, and wherein measuring comprises measuring for the N receive lines at a time with XN receive lines measured in response to the single excitation pulse where X is an integer greater than 1 for temporal sampling such that displacements are not measured for at least some of the receive lines more than once.

5. The non-transitory computer readable storage medium of claim 1 wherein determining the velocity comprises compressively sensing from the displacements, inverse Fourier transforming an output of the compressively sensing, Radon transforming an output of the inverse Fourier transforming, and calculating the velocity from an output of the Radon transforming.

6. The non-transitory computer readable storage medium of claim 1 wherein outputting comprises displaying a value of the velocity for a user selected location.

7. The non-transitory computer readable storage medium of claim 1 wherein determining the velocity comprises determining without identification of a maximum displacement of the displacements for each of the random locations.

8. The non-transitory computer readable storage medium of claim 1 wherein determining the velocity comprises performing compressive sensing on the displacements.

9. The non-transitory computer readable storage medium of claim 1 wherein determining the velocity comprises transforming the displacements.

* * * * *